United States Patent [19]

Perren et al.

[11] Patent Number: 5,053,036
[45] Date of Patent: Oct. 1, 1991

[54] POINT CONTACT BONE COMPRESSION PLATE

[75] Inventors: Stephan N. Perren, Dorf; Fritz Straumann, Waldenburg; Franz Sutter, Niederdorf; Slobodan Tepic, Davos, all of Switzerland

[73] Assignee: Synthes (U.S.A.), Paoli, Pa.

[21] Appl. No.: 492,403

[22] Filed: Mar. 8, 1990

Related U.S. Application Data

[63] Continuation of Ser. No. 247,357, Sep. 21, 1988, abandoned.

[30] Foreign Application Priority Data

Nov. 3, 1987 [WO] PCT Int'l Appl. ... PCT/EP87/00663

[51] Int. Cl.$^5$ ............................................. A61B 17/58
[52] U.S. Cl. .................................. 606/69; 606/71; 606/77
[58] Field of Search ..................... 606/69–71, 606/77; 128/92 YP, 92 YL, 92 YQ, 92 YG, 92 YR, 92 Y, 92 YF

[56] References Cited

U.S. PATENT DOCUMENTS

| 3,463,148 | 8/1969 | Treace | 128/92 YP |
| 4,029,091 | 6/1977 | von Bezold | 606/69 |
| 4,263,904 | 4/1981 | Judet | 128/92 YP X |
| 4,338,926 | 7/1982 | Kummer et al. | 128/92 YP X |
| 4,429,690 | 2/1984 | Angelino-Pievani | 128/92 YP X |
| 4,484,570 | 11/1984 | Sutter et al. | 128/92 YP |
| 4,612,923 | 9/1986 | Kronenthal | 128/92 R |
| 4,651,724 | 3/1987 | Berentey et al. | 128/92 YP |
| 4,683,878 | 8/1987 | Carter | 128/92 YP |
| 4,776,329 | 10/1988 | Treharne | 128/92 YR |
| 4,781,183 | 11/1988 | Casey et al. | 128/92 YP |
| 4,838,252 | 6/1989 | Klaue | 606/69 |

FOREIGN PATENT DOCUMENTS

| 1112803 | 11/1981 | Canada . | |
| 3442004 | 4/1986 | Fed. Rep. of Germany . | |
| 742618 | 1/1933 | France | 128/924 P |
| WO87/00419 | 1/1987 | PCT Int'l Appl. . | |
| 1037911 | 8/1983 | U.S.S.R. | 128/92 YP |

Primary Examiner—Robert A. Hafer
Assistant Examiner—Kevin G. Rooney
Attorney, Agent, or Firm—Davis Hoxie Faithfull & Hapgood

[57] ABSTRACT

A bone plate for use in osteosynthesis having a plurality of contact elements extending from its lower surface so that contact between plate and bone is reduced to the minimum contact needed during attachment of the plate to a bone.

15 Claims, 10 Drawing Sheets

POINT CONTACT BONE COMPRESSION PLATE

This is a continuation of co-pending application Ser. No. 07/247,357, filed on Step. 21, 1988, abandoned.

FIELD OF THE INVENTION

The invention relates to bone plates used as implants in osteosynthesis.

BACKGROUND OF THE INVENTION

In conventional treatment of bone fractures a plate is applied to a fractured bone so as to bridge the fracture. The plate is fixed to the bone by a plurality of screws. When the screws are tightened in the bone, they produce compressive stresses between the plate and the bone. Transmission of a functional load from the bone to the plate and back to the bone is achieved mostly by means of friction corresponding to the compressive stresses.

Usually the screws securing the plate to the bone engage both the near and the far wall of the bone cortex. The cortex receives its blood supply from the periosteum on its outer side and from the endosteum on the inner side. Compression of the plate and bone impedes the blood circulation of the cortex region under the plate. This is believed to increase the chances of infection, which is a major complication of operative fracture treatment.

Dead bone under the plate is in due course remodeled and revascularized. Remodeling starts at the periphery of the unperfused bone and proceeds towards the plate. Porosity within the remodelling bone persists for a long time and reduces bone strength. This situation requires keeping the plate on the bone longer than is needed for the fracture to heal. The use of long screws running first through the near cortex, then through the medullary canal, and through the far cortex may further interfere with blood supply of the fractured bone by cutting through larger blood vessels.

SUMMARY OF THE INVENTION

In accordance with the invention the noted drawbacks of conventional plates are overcome by means of a bone plate for osteosynthesis comprising an elongated body having an upper surface and a lower surface, a plurality of screw holes traversing said body between said surfaces to attach the plate to a bone and a plurality of contact elements extending from the lower surface for contacting the bone during attachment of the plate to the bone.

Use of the plate according to the invention results in reduced damage to bone, particularly damage to the intramedullary vascular system. Moreover, plates according to the invention make it possible to use short screws which can be made self-tapping, without the problems incidental to the use of long self-tapping screws. An additional advantage is that the plate design according to the invention allows for doubling the strength of the bone plate due to reduced screw hole size. Variation in strength and rigidity along the length of the bone plate according to the invention is also much less than in conventional plates. This facilitates plate adaptation to curved bone surfaces.

DESCRIPTION OF THE DRAWINGS

The invention will be disclosed more fully in connection with the accompanying drawings in which.

DETAILED DESCRIPTION

Figure 1:
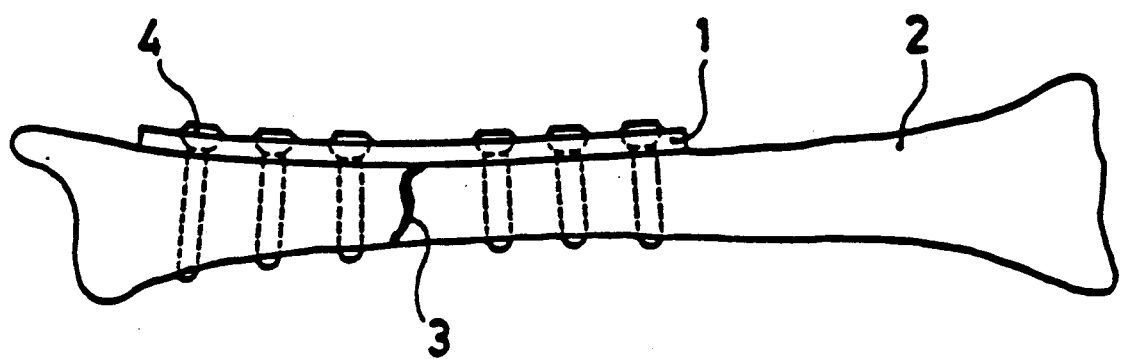
FIG. 1 is a schematic view of a fractured bone with a conventional bone plate.
Figure 2:
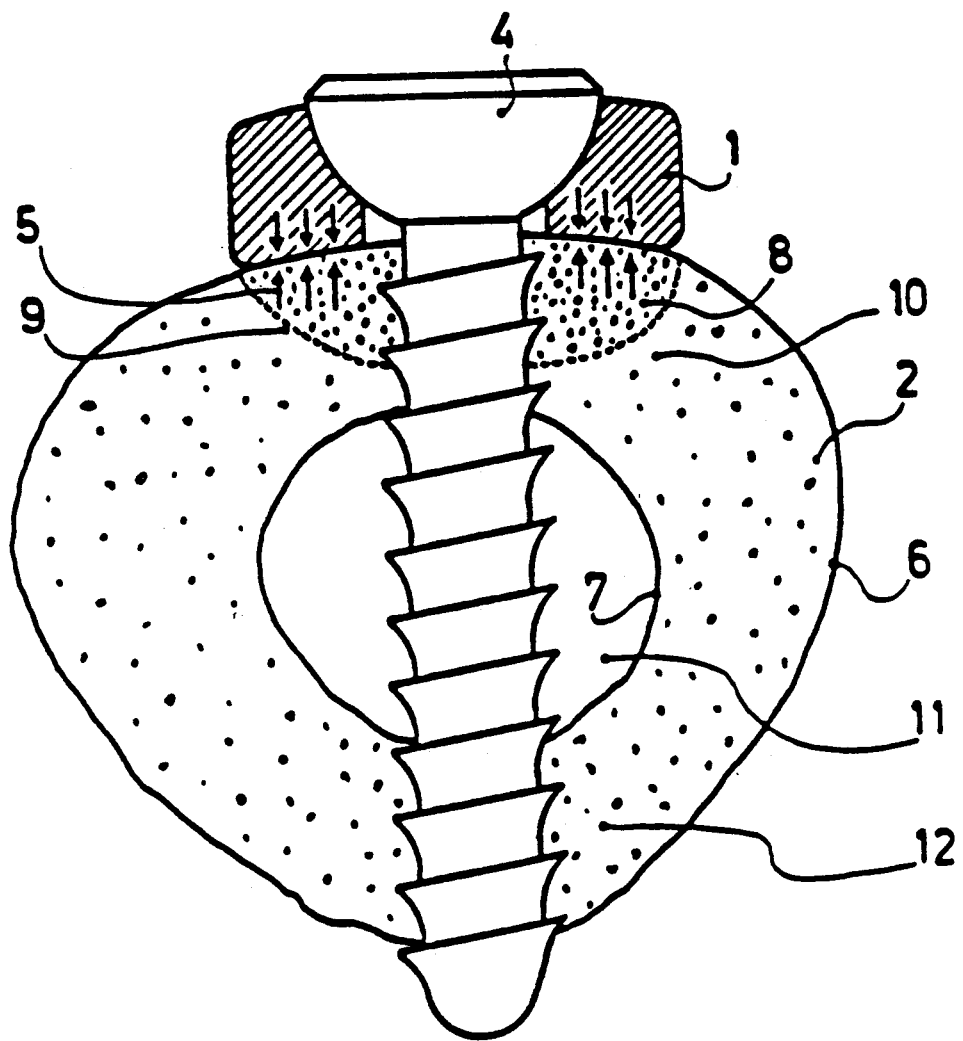
FIG. 2 is a cross-section of the bone plate of FIG. 1.

Referring to FIG. 1, a conventional bone plate 1 for the treatment of bone fractures is fixed to the bone 2 by means of a number of screws 4. Screws 4 are tightened in the bone 2 producing compressive stresses 5 (FIG. 2) between the plate 1 and the bone 2. As shown in FIG. 2, transmission of functional load from the bone 2 to the conventional plate 1 and back to the bone 2 is achieved mostly by means of friction between plate and bone corresponding to the compressive stresses 5, indicated by arrows. Both the near and far walls of the cortex of bone 2 are usually engaged by the screws 4. Bone cortex is supplied by blood from the periosteum, or outer side 6, and from the endosteum or inner side 7. Compressive stresses 5 between the conventional plate 1 and bone 2 impede the blood perfusion of the cortex region 8 under the conventional plate 1. This is believed to increase the likelihood of infection—a major complication of operative fracture treatment.

Dead bone in region 8 is in due course remodelled and revascularized. This remodelling activity starts at periphery 9 of the unperfused part of the bone and proceeds towards plate 1. Porosity within the remodelling bone persists for a long time and reduces bone strength, particularly in fatigue. It is therefore necessary to keep the conventional plate 1 on the bone for a period longer than is needed for the fracture to heal. Long screws 4, by running first through the near cortex 10, then through the medullary canal 11 and through the far cortex 12, may further interfere with blood supply to the fractured bone by cutting through larger blood vessels.

Figure 3:
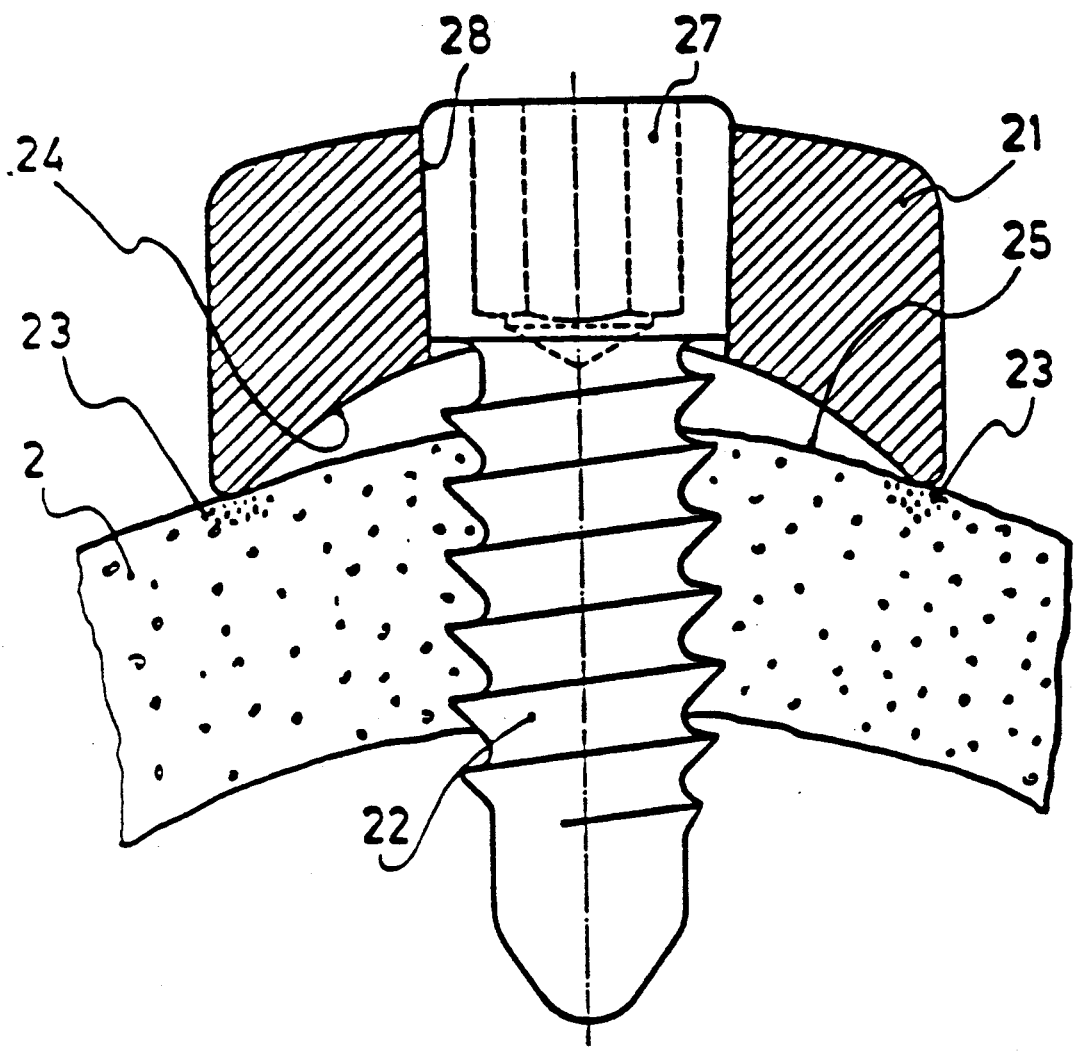
FIG. 3 is a cross-section of a bone plate according to the invention with short screws.
Figure 4:
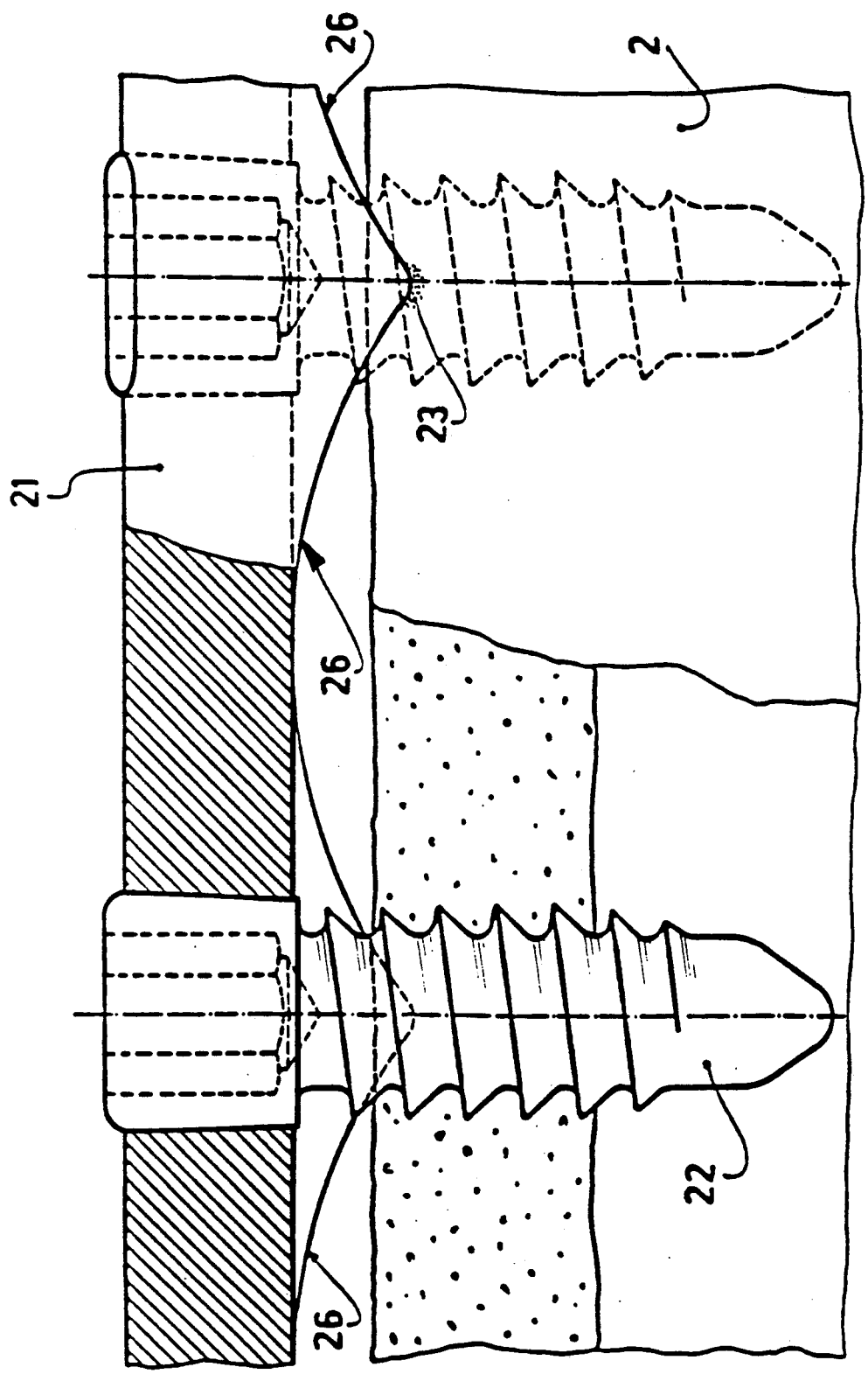
FIG. 4 is a view in side elevation and partly in vertical section of the bone plate of FIG. 3.

Referring now to FIG. 3, a plate 21 according to the invention is attached to the bone 2 by means of a plurality of short screws 22, which are inserted through conical screw holes 28 in the plate. The undersurface of the plate is shaped so as to permit contact with the bone only at points 23. In a preferred embodiment, this is achieved by arching the underside of the plate 24 at a transverse curvature of smaller radius than that of the bone's outer contour 25. In the longitudinal direction, as shown in FIG. 4, the underside of the plate is also shaped with a plurality of arches 26 between the screws 22. Therefore, the only contact between plate and bone is at points 23.

The area of contact with the bone is reduced to the minimum practicable. Preferably this is less than 5% of the total area of the lower surface of the plate and most preferably less than 2%.

As shown in FIG. 3, the plate according to the invention may be attached to the bone by a screw 22 having a conical head 27 which upon insertion locks safely in a conical hole 28 of the plate 21. The cone angle of the screw is the same as the cone angle of the screw hole. Since the angle is very small, the plate does not come loose and fall down onto the bone. In other words, the angle of the cone on the screw head 27 is smaller than the friction angle. The friction angle is the angle at which a surface must be inclined so that a body with a plane surface is just about it slide down it. In the context of the present invention, the fiction angle is the angle at which the plate (were it not for the contact points) would be about to slide down the head of the screw. The taper of the cone is preferably between 1:5 and 1:20.

The use of short screws 22 in place of conventional long screws is made possible because screw 22 can be locked into the plate 21. This prevents tilting of the screw 22 within the cortex of bone 2. Loads between the bone 2 and the plate 21 are transferred directly through the screws 22 which now act as pegs (under shear) rather than anchors (under tension), which would be the case if a long screw reached through the medullary canal to the far cortex. In addition to reducing damage to bone 2 and in particular to the intramedullary vascular system, short screws 22 can be made self-tapping without the problems incidental to the use of long self-tapping screws.

The undercutting of the plate 21 with arches 24 in the transverse direction and arches 26 in the longitudinal direction has advantages in addition to reducing the plate-bone contact to points 23. The strength and rigidity of conventional plates is lowest at the sections which have screw holes. Overall plate strength is limited by the weakest section. While keeping outer dimensions similar to those of a conventional plate, the plate design according to the invention allows for doubling plate strength. This is largely due to the reduced size of the screw holes. Variation of strength and rigidity along the plate is much smaller than in conventional plates. These characteristics facilitate plate adaptation to curved bone surfaces.

Figure 5:
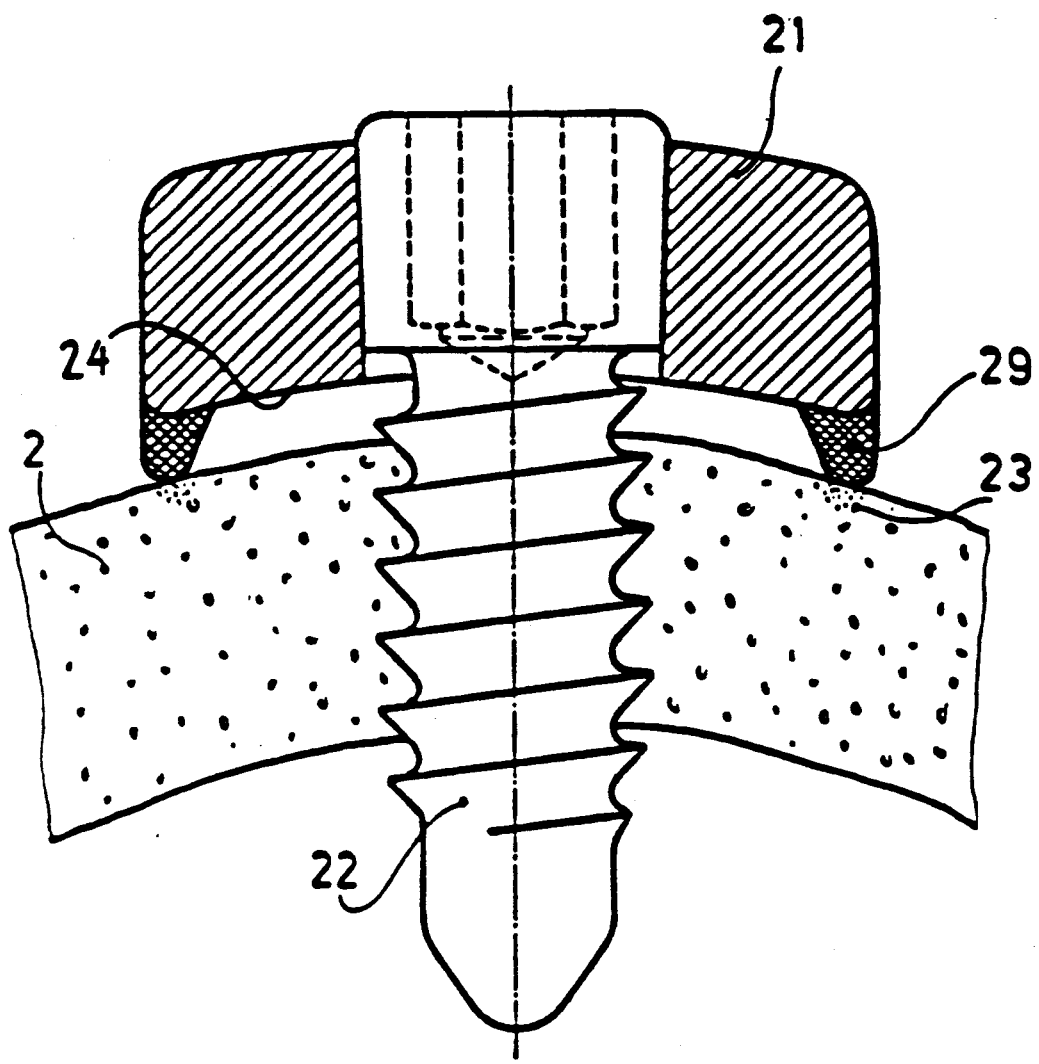
FIG. 5 is a cross-section of a bone plate according to the invention with resorbable studs at the plate undersurface.

FIG. 5 shows another embodiment of the invention in which contact between the plate 21 and the bone 22 is reduced. Small studs 29 are added to the undersurface of the plate. These studs may be made from a material which is resorbable or even dissolvable in the body (e.g. polysaccacharides), so that after the plate is positioned they will disappear entirely. This is possible because the studs are only necessary to support the plate during the procedure of inserting and locking the screw 22 into the plate 21.

Figure 6:
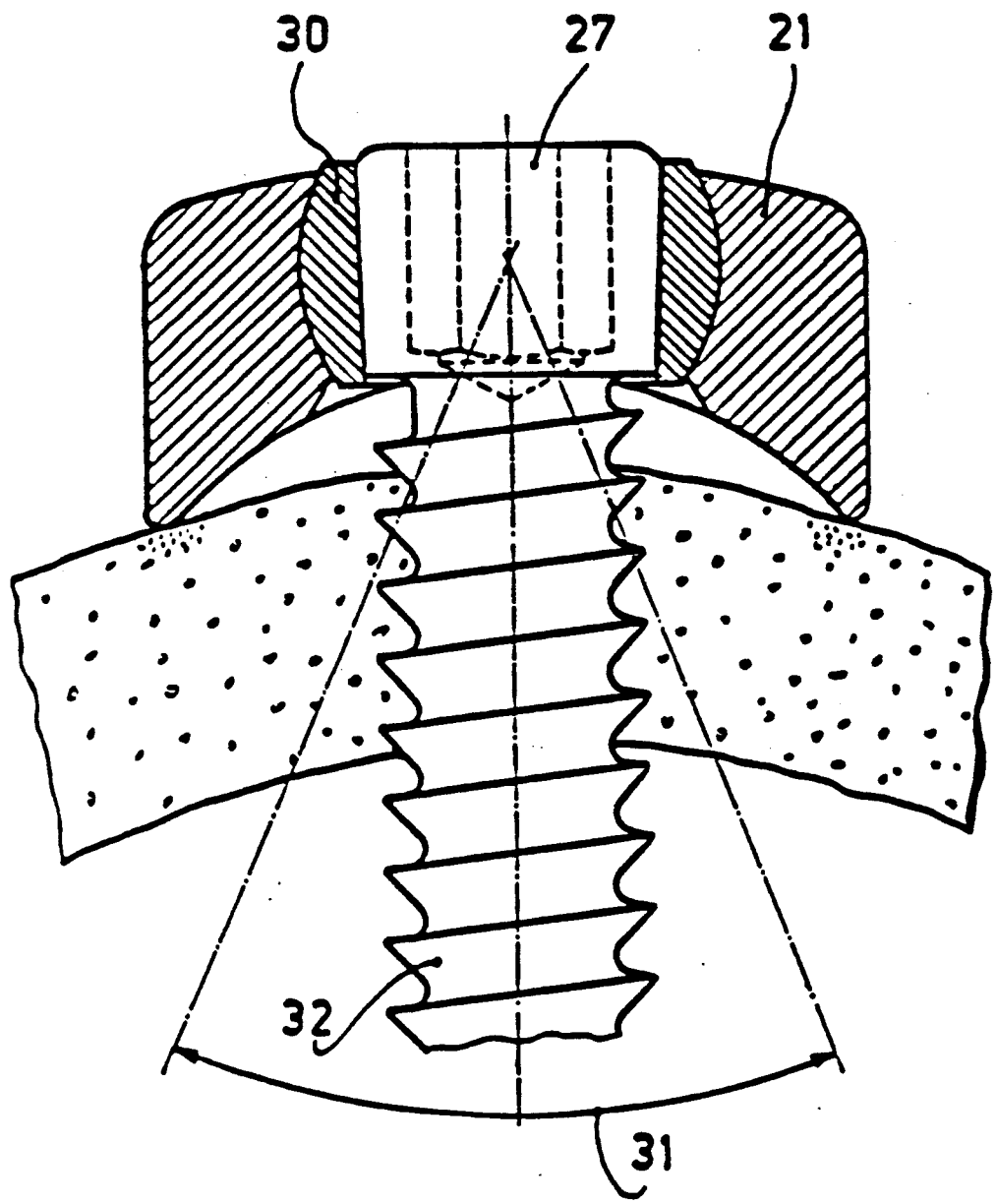
FIG. 6 is a cross-section of a bone plate according to the invention with an expandable spherical insert.
Figure 6A:
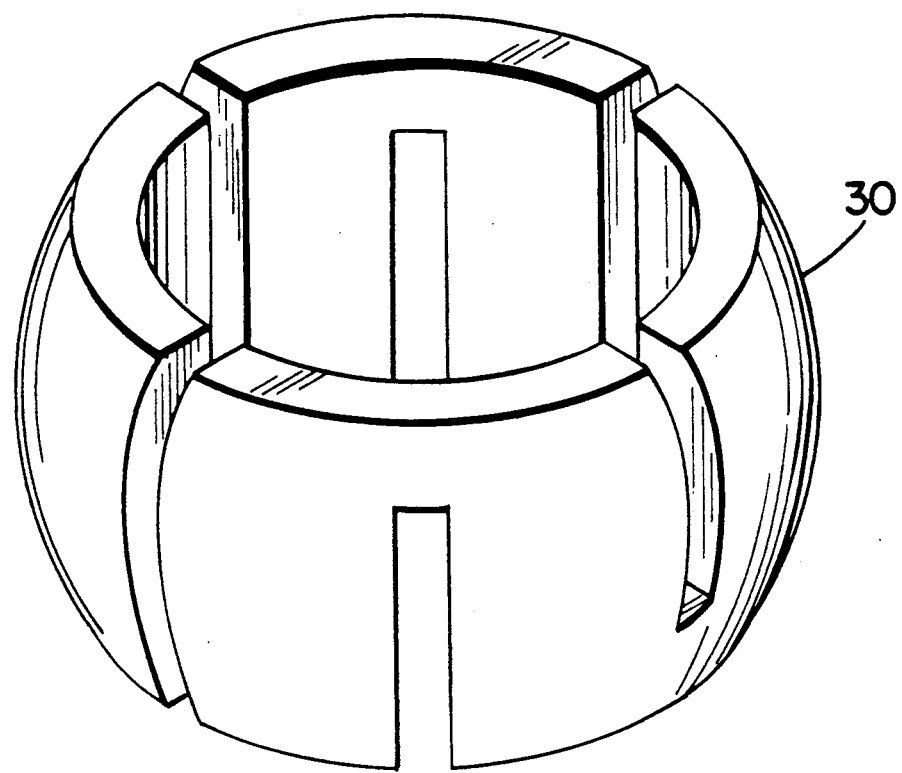
FIG. 6A is a perspective of the spherical insert of FIG. 6.

FIG. 6 shows a plate 21 according to the invention combined with a long screw 32 which may be locked into the plate 21 via a spherical insert 30. The screw is thus given substantial freedom of angular placement as indicated at 31. As it is forced into sphere 30, (see FIG. 6A) the conical head 27 of the screw 32 compresses the slotted sphere 30 against the plate, locking itself and the sphere 30 in the plate 21. The taper of the cone angle is again smaller than the friction angle, preferably between 1:5 and 1:20.

Figure 7:
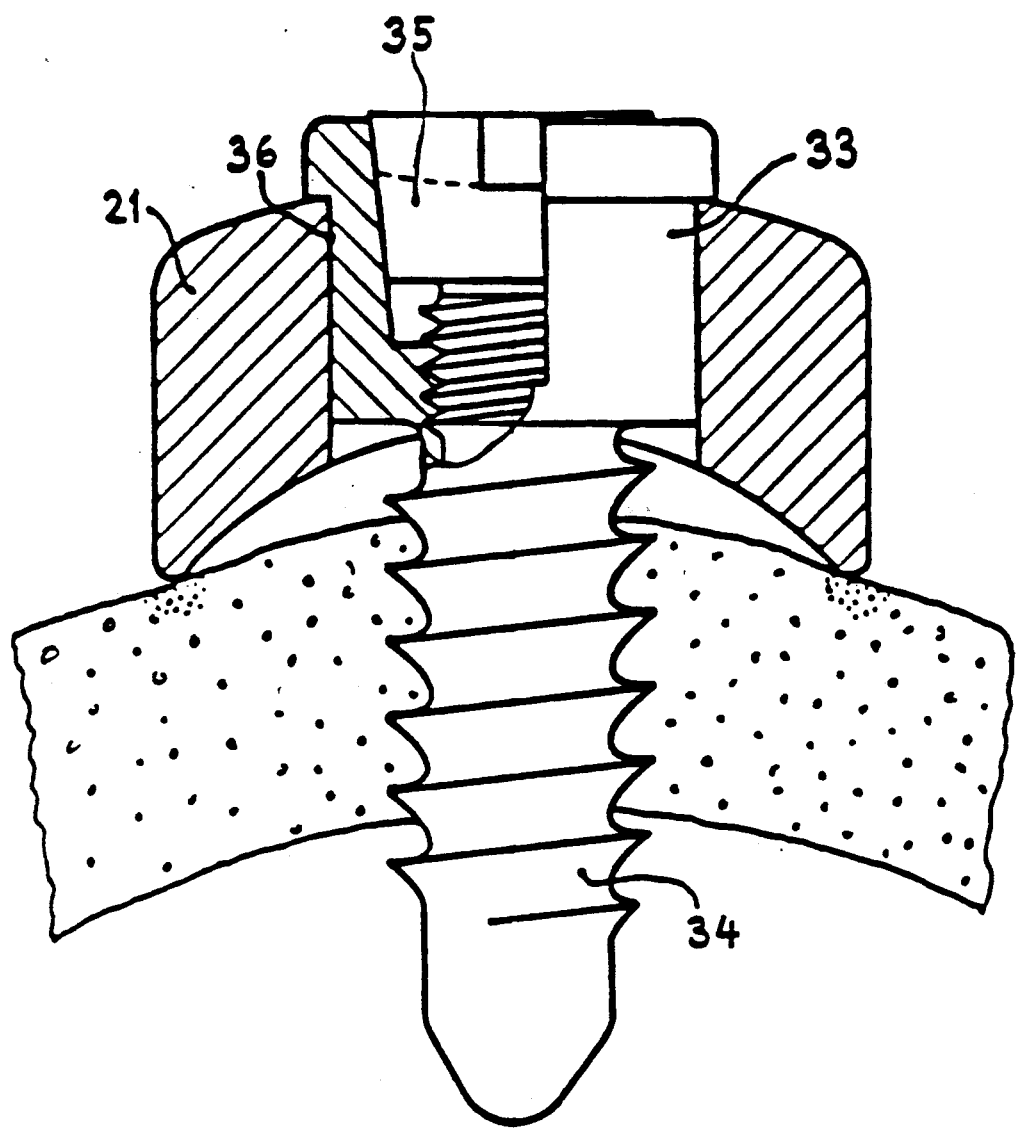
FIG. 7 is a cross-section of a bone plate according to the invention with a screw head expandable by a conical insert.

FIG. 7 shows another embodiment of the invention where the locking of the screw 34 in the plate 21 is achieved by the conical insert 35, which when driven down expands the slotted screw-head 33, thereby forming a rigid connection at the cylindrical interface 36.

Figure 8:
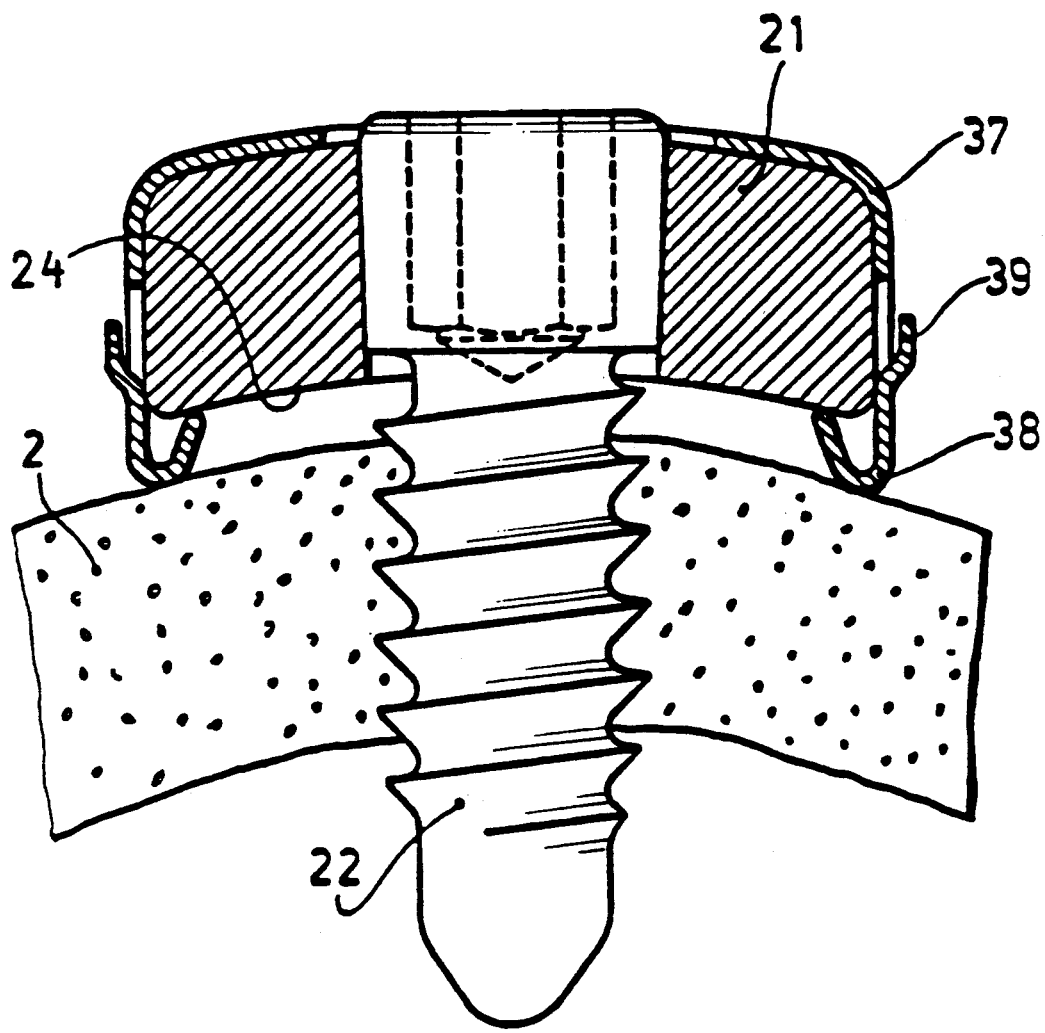
FIG. 8 is a cross-section of a bone plate according to the invention with removable clip-on springs.
Figure 9:
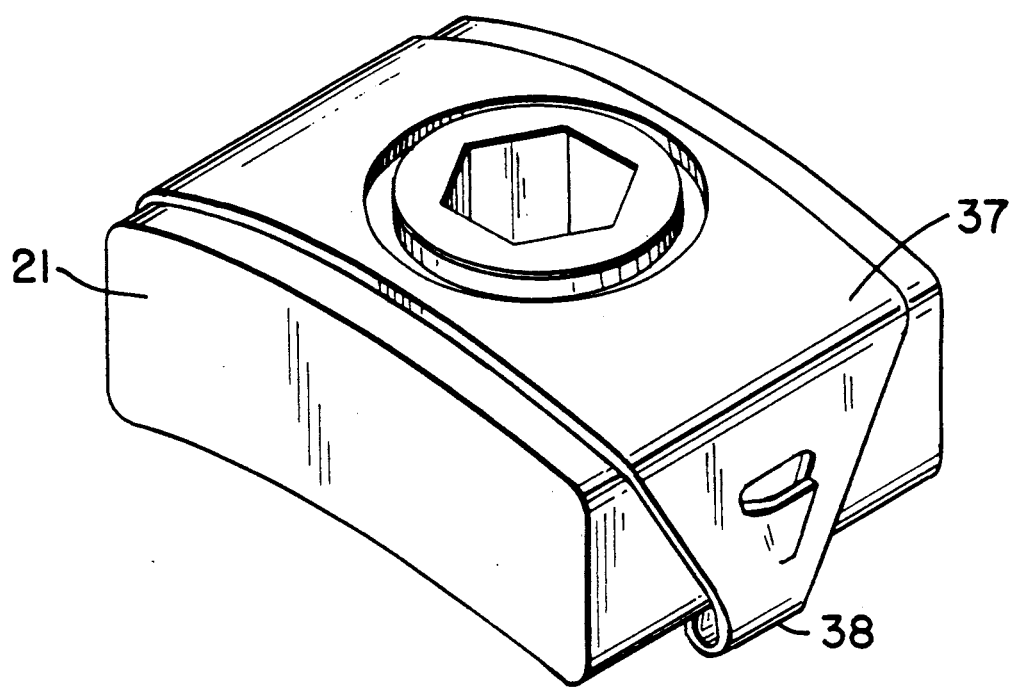
FIG. 9 is a perspective view of a section of the bone plate according to FIG. 8 showing a clip-on spring.

FIGS. 8 and 9 show a further embodiment of the invention where the reduced plate contact with the bone 2 is achieved through removable clip-on springs 37 which provide stud-like extensions 38 on the undersurface of plate 21. Springs 37 may be removed following insertion and locking of screw 22 in the plate 21. Hooks 39 facilitate removal following screw tightening.

The plate may be constructed with one or more self-compressing screw holes of the type described in U.S. Pat. No. Re. 31,628.

What is claimed is:

1. A compression plate for osteosynthesis, said plate having a longitudinal axis, an upper surface, a lower surface and a plurality of screw holes spaced in the direction of the longitudinal axis, said lower surface being arched concavely transversely to the longitudinal axis of the plate, in combination with open sections along the side edges of the plate between the screw holes, said open sections, with the concave lower surface of the plate, forming studs along the side edges of the lower surface for contact with a bone.

2. A compression plate according to claim 1 wherein said screw holes are conical and traverse said plate between said upper and lower surfaces such that the narrow end of the cone is towards the lower surface, said holes adapted to receive screws having conical heads of a predetermined cone angle, such that the plate will not slide down the heads of the screws.

3. A bone plate according to claim 2 wherein the taper of the conic section is in the range of 1:5 to 1:20.

4. A bone plate according to claim 1 wherein one screw hole is a self-compressing hole.

5. A bone plate according to claim 1 wherein the contact elements are less than 5% of the total area of the lower surface of the plate.

6. A bone plate according to claim 1 wherein the contact elements are less than 2% of the total area of the lower surface of the plate.

7. A metallic compression plate for osteosynthesis, said plate having a longitudinal axis, an upper surface, a lower surface, side walls joining said upper and lower surfaces and a plurality of screw holes spaced in the direction of said longitudinal axis, in combination with a plurality of individual, non-metallic, support studs attached to the lower surface of the plate at the sides of said lower surface and longitudinally spaced in the direction of said axis, said studs providing bone contact, at selected points along the sides of said plate, and spacing the central portion of the lower surface of said plate along the longitudinal axis from the bone.

8. A bone plate according to claim 7 wherein the contact elements comprise studs made of material which is resorbable or dissolvable in body fluids.

9. A bone plate assembly comprising a compression bone plate and a plurality of bone screws for attaching said plate to a bone, said plate having a longitudinal axis, an upper surface, a lower surface and a plurality of screw holes for receiving said screws, spaced in the direction of the longitudinal axis, said lower surface being arched concavely transversely to the longitudinal axis of the plate, in combination with open sections along the side edges of the plate between the screw holes, said open sections, with the concave undersurface of the plate, forming studs for bone contact along the side edges of the lower surface of the plate.

10. A bone plate assembly according to claim 9 wherein the screws the heads which are expandable by means of a body inserted into said head.

11. A bone plate assembly according to claim 9 and comprising a body fitted into the screw hole, said body being expandable by a conical screw head which has a cone angle smaller than the resulting friction angle.

12. A bone plate assembly according to claim 11 wherein the taper of the cone angle is in the range of 1:5 to 1:20.

13. A bone plate assembly according to claim 9 wherein said screws are of a length that permits engagement of the screw with only one side of the bone cortex.

14. A compression plate for osteosynthesis, said plate having a longitudinal axis, an upper surface, a lower surface and a plurality of screw holes spaced in the direction of the longitudinal axis, said lower surface being arched concavely, transversely to the longitudinal axis of the plate, in combination with arcuate cut out sections between the holes, the intersection of surfaces formed by said cut out sections and the concave lower surface of the plate forming studs for bone contact.

15. A compression plate for osteosynthesis, said plate having a longitudinal axis, an upper surface, a concave lower surface, side walls joining said upper and lower surfaces and a plurality of screw holes spaced in the direction of said longitudinal axis, in combination with a plurality of clips removably attached to said plate and spaced along the length of said plate, each of said clips extending across the upper surface of the plate, down the side walls thereof and having elements extending below the lower surface of said plate to provide a limited area of bone contact.

* * * * *

(12) EX PARTE REEXAMINATION CERTIFICATE (5746th)
United States Patent
Perren et al.

(10) Number: US 5,053,036 C1
(45) Certificate Issued: Apr. 24, 2007

(54) POINT CONTACT BONE COMPRESSION PLATE

(75) Inventors: Stephan N. Perren, Dorf (CH); Fritz Straumann, Waldenburg (CH); Franz Sutter, Niederdorf (CH); Slobodan Tepic, Davos (CH)

(73) Assignee: Synthes (U.S.A.), Paoli, PA (US)

Reexamination Request:
No. 90/006,558, Mar. 6, 2003

Reexamination Certificate for:
Patent No.: 5,053,036
Issued: Oct. 1, 1991
Appl. No.: 07/492,403
Filed: Mar. 8, 1990

Related U.S. Application Data

(63) Continuation of application No. 07/247,357, filed on Sep. 21, 1988, now abandoned.

(30) Foreign Application Priority Data

Nov. 3, 1987 (WO) .............................. PCT/EP87/00663

(51) Int. Cl.
*A61B 17/56* (2006.01)
*A61B 17/58* (2006.01)
*A61F 2/30* (2006.01)

(52) U.S. Cl. .............................. 606/69; 606/71; 606/77
(58) Field of Classification Search ........................ None
See application file for complete search history.

(56) References Cited

U.S. PATENT DOCUMENTS

| | | | |
|---|---|---|---|
| 1,105,105 A | 7/1914 | Sherman | |
| 4,263,904 A | 4/1981 | Judet | 128/92 |
| 4,338,926 A | 7/1982 | Kummer et al. | 128/92 |
| 4,364,382 A | 12/1982 | Mennen | 128/92 |
| RE31,628 E | 7/1984 | Allgower et al. | 128/92 |
| 4,484,570 A | 11/1984 | Sutter et al. | 128/92 |

OTHER PUBLICATIONS

Defendant DePuy Ace Medical Company's Motion for Summary Judgment of Non–Infringement or Invalidity and supporting documents filed Oct. 15, 1999 on behalf of defendant Deputy Ace Medical Company in *Synthes (U.S.A.)* v. *DePuy Ace Medical Company* 98–CV–2687.

Synthes' Motion for Claim Interpretation and for Summary Judgment of Infringement and Validity of Claims 4 and 14, Synthes' Memorandum in Support of Its Motion for Claim Interpretation and for Summary Judgment of Infringement and Validity of Claims 4 and 14. Declaration of Leo Merkin in Support of Synthes' Motion for Claim Interpretation and for Summary Judgment of Infringement and Validity of Claims 4 and 14, Proposed Order and Notice of Filing Under Seal, filed Oct. 15, 1999 on behalf of plaintiff Synthes (U.S.A.) in *Synthes (U.S.A.)* v. *DePuy Ace Medical Company* 98–CV–2687.

DePuy Ace Medical's Response in Opposition to Synthes' Motion for Claim Construction and Summary Judgment of Infringement and Validity of Claims 4 and 14, filed Nov. 1, 1999 on behalf of defendant Deputy Ace Medical Company in *Synthes (U.S.A.)* v. *DePuy Ace Medical Company* 98–CV–2687.

Synthes' Memorandum in Opposition to Depuy Ace's Motion for Summary Judgment or Non–Infringement of Invalidity and supporting documents filed Nov. 1, 1999 on behalf of plaintiff Synthes (U.S.A.) in *Synthes (U.S.A.)* v. *DePuy Ace Medical Company* 98–CV–2687.

Memorandum and Order denying Defendant's Motion for Summary Judgment as to Non–Infringement and Invalidity and denying Plaintiff's Motion for Summary Judgment as to Infringement and Validity of Claims 4 and 14, dated Nov. 29, 1999, by Ronald L. Buckwalter, Judge, U.S. District Court for the Eastern District of Pennsylvania, in *Synthes (U.S.A.)* v. *DePuy Ace Medical Company* 98–CV–2687.

(Continued)

*Primary Examiner*—Beverly M. Flanagan

(57) ABSTRACT

A bone plate for use in osteosynthesis having a plurality of contact elements extending from its lower surface so that contact between plate and bone is reduced to the minimum contact needed during attachment of the plate to a bone.

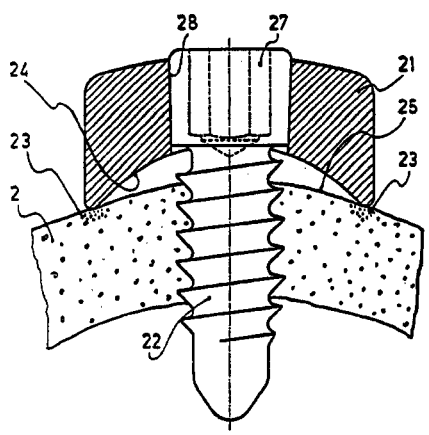

OTHER PUBLICATIONS

Synthes' Reply Memorandum in Support of Its Motion for Summary Judgment of Infringement and Validity of Claims 4 and 14, filed Nov. 30, 1999 on behalf of plaintiff Synthes (U.S.A.) in *Synthes (U.S.A.)* v. *DePuy Ace Medical Company* 98–CV–2687.

Order dismissing Action, dated May 8, 2000, by Michael E. Kunz, Clerk, U.S. District Court for the Eastern District of Pennsylvania, in *Synthes (U.S.A.)* v. *DePuy Ace Medical Company* 98–CV–2687.

Stipulated Dismissal and Order, dated Jul. 5, 2000, by Ronald L. Buckwalter, Judge, U.S. District Court for the Eastern District of Pennsylvania, in *Synthes (U.S.A.)* v. *DePuy Ace Medical Company* 98–CV–2687.

Vattolo, M., "The Effects of Grooves in Osteosynthesis Plates on the Restructuring of the Corticalis" dated 1986 (in German).

Vattolo, M., "The Effects of Grooves in Osteosynthesis Plates on the Restructuring of the Corticalis" dated 1986 (translation into English with translation certification) (with declaration dated Feb. 27, 2003 from the Swiss National Library; and cover page and p. 37 from the Swiss National Bibliography dated Jan. 1, 1987).

Raveh et al., "New Concepts in the Reconstruction of Mandibular Defects Following Tumor Resection" J Oral Maxillofac Surg 41:3–16, 1983.

Raveh et al., "Use of the Titanium–coated Hollow Screw and Reconstruction Plate System in Bridging of Lower Jaw Defects" J Oral Maxillofac Surg 42:281–294, 1984.

Sutter et al., "Titantium–Plasma–Coated Hollow Screw and Reconstruction Plate System (THRP) for Bridging Jaw Defects" Der Chirurg 55:741–748, 1984 (in German).

Sutter et al., "Titantium–Plasma–Coated Hollow Screw and Reconstruction Plate System (THRP) for Bridging Jaw Defects" Der Chirurg 55:741–748, 1984 (translation into English with translation certification).

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 7 and 15 is confirmed.

Claim 5 is cancelled.

Claims 1, 3, 4, 6, 8–14 are determined to be patentable as amended.

Claim 2, dependent on an amended claim, is determined to be patentable.

New claims 16–58 are added and determined to be patentable.

1. A compression plate for osteosynthesis, said plate having a longitudinal axis, an upper surface, a lower surface and a plurality of screw holes spaced in the direction of the longitudinal axis, said lower surface being arched concavely transversely to the longitudinal axis of the plate, in combination with open sections along the side edges of the plate between the screw holes, said open sections, with the concave lower surface of the plate, forming studs along the side edges of the lower surface for contact with a bone, *wherein the studs for bone contact are less than 5% of the total area of the lower surface of the plate.*

3. A [bone] *compression* plate according to claim 2 wherein the taper of the conic section is in the range of 1:5 to 1:20.

4. A [bone] *compression* plate according to claim 1 wherein one screw hole is a self-compressing hole.

6. A [bone] *compression* plate according to claim 1 wherein the contact elements are less than 2% of the total area of the lower surface of the plate.

8. A [bone] *compression* plate according to claim 7 wherein the contact elements comprise studs made of material which is resorbable or dissolvable in body fluids.

9. A [bone] *compression* plate assembly comprising a compression bone plate and a plurality of bone screws for attaching said plate to a bone, said plate having a longitudinal axis, an upper surface, a lower surface and a plurality of screw holes for receiving said screws, spaced in the direction of the longitudinal axis, said lower surface being arched concavely transversely to the longitudinal axis of the plate, [in combination with] open sections along the side edges of the plate between the screw holes, *said open sections forming concavities in the lower surface of the plate, and* said open sections, *in combination* with the concave undersurface of the plate, forming studs for bone contact along the side edges of the lower surface of the plate, *wherein the studs for bone contact are less than 5% of the total area of the lower surface of the plate.*

10. A [bone] *compression* plate assembly according to claim 9 wherein the screws [the] *have* heads which are expandable by means of a body inserted into said head.

11. A [bone] *compression* plate assembly according to claim 9 and comprising a body fitted into the screw hole, said body being expandable by a conical screw head which has a cone angle smaller than the resulting friction angle.

12. A [bone] *compression* plate assembly according to claim 11 wherein the taper of the cone angle is in the range of 1:5 to 1:20.

13. A [bone] *compression* plate assembly according to claim 9 wherein said screws are of a length that permits engagement of the screw with only one side of the bone cortex.

14. A compression plate for osteosynthesis, said plate having a longitudinal axis, an upper surface, a lower surface and a plurality of screw holes spaced in the direction of the longitudinal axis, said lower surface being arched concavely, transversely to the longitudinal axis of the plate, [in combination with] arcuate cut out sections between the holes, *said arcuate cut out sections forming concavities in the lower surface of the plate, and* the intersection of surfaces formed by said cut out sections and the concave lower surface of the plate forming studs for bone contact, *wherein the studs for bone contact are less than 5% of the total area of the lower surface of the plate.*

*16. A compression plate comprising:*
*a longitudinal axis;*
*an upper surface;*
*a lower surface arched concavely transversely to the longitudinal axis;*
*a plurality of screw holes spaced apart in the direction of the longitudinal axis;*
*side walls joining the upper and lower surfaces, the side walls including open sections between the screw holes, the open sections extending transversely and forming undercuts in at least a portion of the concave lower surface of the plate,*
*wherein the undercuts, in combination with the transverse concave arching of the lower surface of the plate, form studs for bone contact which comprise less than 5% of the total area of the lower surface of the plate.*

*17. The compression plate of claim 16, wherein the studs for bone contact are less than 2% of the total area of the lower surface of the plate.*

*18. The compression plate of claim 16, further comprising the side walls being substantially planar.*

*19. The compression plate of claim 16, further comprising at least one of the open sections having an arcuate shape.*

*20. The compression plate of claim 16, wherein the two screw holes are elongated screw holes.*

*21. The compression plate of claim 20, wherein the elongated screw holes are self-compressing holes.*

*22. The compression plate of claim 16, wherein at least one of the open sections extends from one side wall to the other side wall.*

*23. The compression plate of claim 22, wherein further all of the open sections extend from one side wall to the other side wall.*

24. The compression plate of claim 16, wherein at least one open section does not intersect the upper surface of the plate.

25. The compression plate of claim 24, wherein further none of the open sections intersects the upper surface of the plate.

26. A compression plate comprising:
a longitudinal axis;
an upper surface;
a lower surface arched concavely transversely to the longitudinal axis;
a plurality of self-compressing screw holes spaced apart in the direction of the longitudinal axis;
side walls joining the upper and lower surfaces, the side walls including open sections extending transversely therethrough, forming undercuts in at least a portion of the concave lower surface of the plate, the position of the open sections in the direction of the longitudinal axis being between self-compression screw holes;
wherein the undercuts, in combination with the transversely concavely arched lower surface of the plate, form studs for bone contact which comprises less than 5% of the total area of the lower surface of the plate.

27. The compression plate of claim 26, wherein the studs for bone contact are less than about 2% of the total area of the lower surface of the plate.

28. The compression plate of claim 26, further comprising the side walls being substantially planar.

29. The compression plate of claim 26, further comprising at least one of the open sections having an arcuate shape.

30. The compression plate of claim 26, wherein a portion of the at least one of the open sections is located along the longitudinal axis.

31. The compression plate of claim 26, wherein at least one of the open sections extends from one side wall to the other side wall.

32. The compression plate of claim 31, wherein further all of the open sections extend from one side wall to the other side wall.

33. The compression plate of claim 26, wherein at least one open section does not intersect the upper surface of the plate.

34. The compression plate of claim 33, wherein further none of the open sections intersects the upper surface of the plate.

35. A compression plate comprising:
a longitudinal axis;
an upper surface;
a lower surface arched concavely transversely to the longitudinal axis;
a plurality of elongated screw holes spaced apart in the direction of the longitudinal axis;
side walls joining the upper and lower surfaces, the side walls including open sections extending transversely therethrough, forming undercuts in at least a portion of the concave lower surface of the plate, the open sections lying between elongated screw holes when the compression plate if viewed in a direction looking toward one of the side walls;
wherein the undercuts, in combination with the concave arching of the lower surface of the plate, form studs for bone contact extending downwards from the lower surface of the plate and below the side walls, and wherein the studs for bone contact have a bone contact area less than 5% of the total area of the lower surface of the plate.

36. The compression plate of claim 35, wherein the studs for bone contact have a bone contact area less than about 2% of the total area of the lower surface of the plate.

37. The compression plate of claim 35, further comprising the side walls being substantially planar.

38. The compression plate of claim 35, further comprising at least one of the open sections having an arcuate shape.

39. The compression plate of claim 35, wherein a portion of the at least one of the open sections is located along the longitudinal axis.

40. The compression plate of claim 35, wherein the elongated screw holes are self-compressing holes.

41. The compression plate of claim 35, wherein at least one of the open sections extends from one side wall to the other side wall.

42. The compression plate of claim 41, wherein further all of the open sections extend from one side wall to the other side wall.

43. The compression plate of claim 35, wherein at least one open section does not intersect the upper surface of the plate.

44. The compression plate of claim 43, wherein further none of the open sections intersects the upper surface of the plate.

45. A compression plate comprising:
a longitudinal axis;
an upper surface;
a lower surface archec concavely transversely to the longitudinal axis;
a plurality of self-compressing screw holes spaced apart in the direction of the longitudinal axis;
side walls joining the upper and lower surfaces, the side walls including open sections between the screw holes, the open sections extending transversely and forming undercuts in at least a portion of the concave lower surface of the plate;
wherein the undercuts, in combination with the transverse concave arched lower surface of the plate, form studs for bone contact having a bone contact area less than 5% of the total area of the lower surface of the plate, extending downward from the lower surface of the plate and below the side walls.

46. The compression plate of claim 45, wherein the studs for bone contact have a bone contact area less than about 2% of the total area of the lower surface of the plate.

47. The compression plate of claim 45, further comprising the side walls being substantially planar.

48. The compression plate of claim 45, further comprising at least one of the open sections having an arcuate shape.

49. The compression plate of claim 45, wherein at least one of the open sections extends from one side wall to the other side wall.

50. The compression plate of claim 49, wherein further all of the open sections extend from one side wall to the other side wall.

51. The compression plate of claim 45, wherein at least one open section does not intersect the upper surface of the plate.

52. The compression plate of claim 51, wherein further none of the open sections intersects the upper surface of the plate.

53. A compression plate comprising:
a longitudinal axis;
an upper surface;
a lower surface arched concavely transversely to the longitudinal axis;

a plurality of self-compressing screw holes spaced apart in the direction of the longitudinal axis;

side walls joining the upper and lower surfaces, the side walls including open sections between the screw holes, the open sections being arched transversely to the longitudinal axis and forming undercuts in at least a portion of the concave lower surface of the plate, all of the open sections extending from one side wall to the other side wall and none of the open sections intersecting the upper surface of the plate;

wherein the undercuts in the concave lower surface of the plate form studs for bone contact extending downwards from the lower surface of the plate and below the side walls, and wherein the studs for bone contact comprise less than 5% of the total area of the lower surface of the plate.

54. The compression plate of claim 53, wherein the studs for bone contact are less than about 2% of the total area of the lower surface of the plate.

55. A compression plate comprising:

a longitudinal axis;

an upper surface having side edges;

a lower surface, having side edges and being arched concavely transversely to the longitudinal axis;

a vertical axis perpendicular to the longitudinal axis and in the direction from the lower surface towards the upper surface;

a plurality of self-compression screw holes spaced apart in the direction of the longitudinal axis;

side walls joining the upper and lower surfaces, the side walls having a height defined by the distance between the side edges of the upper and lower surfaces;

a widthwise axis perpendicular to the longitudinal axis and in the direction from one side wall to the other side wall;

wherein each side wall includes a plurality of open sections extending therethrough in the widthwise direction, the open sections extending vertically over a portion, but not all, of the height of the side walls, and the open sections further forming undercuts in at least a portion of the concave lower surface of the plate, each open section being between two self-compressed screw holes;

wherein the undercuts in the concave lower surface of the plate form studs for bone contact extending downwards from the lower surface of the plate and below the side walls, and wherein the studs for bone contact comprise less than 5% of the total area of the lower surface of the plate.

56. The compression plate of claim 55, wherein the studs for bone contact are less than about 2% of the total area of the lower surface of the plate.

57. A compression plate for osteosynthesis, said plate having a longitudinal axis, an upper surface, a lower surface and a plurality of screw holes spaced in the direction of the longitudinal axis, said lower surface being arched concavely transversely to the longitudinal axis of the plate, in combination with open sections aoong the side edges of the plate between the screw holes, said open sections, with the concave lower surface of the plate, forming studs along the side edges of the lower surface for contact with a bone, wherein the contact elements are less than 5% of the total area of the lower surface of the plate.

58. A compression plate for osteosynthesis, said plate having a longitudinal axis, an upper surface, a lower surface and a plurality of screw holes spaced in the direction of the longitudinal axis, said lower surface being arched concavely transversely to the longitudinal axis of the plate, in combination with open sections along the side edges of the plate between the screw holes, said open sections, with the concave lower surface of the plate, forming studs along the side edges of the lower surface for contact with a bone, wherein the contact elements are less than 2% of the total area of the lower surface of the plate.

* * * * *